(12) United States Patent
Su

(10) Patent No.: US 7,669,478 B2
(45) Date of Patent: Mar. 2, 2010

(54) ULTRASONIC DRIVING DEVICE WITH MULTI-FREQUENCY SCANNING

(75) Inventor: Jong-Jeng Su, Taichung (TW)

(73) Assignee: ZMI Electronics Ltd. (TW)

( * ) Notice: Subject to any disclaimer, the term of this patent is extended or adjusted under 35 U.S.C. 154(b) by 469 days.

(21) Appl. No.: 11/549,245

(22) Filed: Oct. 13, 2006

(65) Prior Publication Data

US 2008/0087092 A1    Apr. 17, 2008

(51) Int. Cl.
*G01N 29/34* (2006.01)
(52) U.S. Cl. ...................................... 73/632
(58) Field of Classification Search .............. 73/632
See application file for complete search history.

(56) References Cited

U.S. PATENT DOCUMENTS

| | | | | |
|---|---|---|---|---|
| 5,834,871 A * | 11/1998 | Puskas | ................ | 310/316.02 |
| 6,181,051 B1 * | 1/2001 | Puskas | ................ | 310/316.01 |
| 6,243,323 B1 * | 6/2001 | Li | ................ | 367/138 |
| 6,433,460 B1 * | 8/2002 | Puskas | ................ | 310/317 |
| 6,822,372 B2 * | 11/2004 | Puskas | ................ | 310/317 |
| 6,875,401 B1 * | 4/2005 | Suzuki et al. | ................ | 422/63 |
| 7,211,928 B2 * | 5/2007 | Puskas | ................ | 310/317 |
| 2006/0054182 A1 * | 3/2006 | Korbler et al. | ................ | 134/1 |

FOREIGN PATENT DOCUMENTS

WO    WO 95/22065    *    8/1995

* cited by examiner

*Primary Examiner*—Hezron Williams
*Assistant Examiner*—Rose M Miller
(74) *Attorney, Agent, or Firm*—Ostrolenk Faber LLP

(57) ABSTRACT

An ultrasonic driving device with multi-frequency scanning that includes a signal generating module, an output module, and an ultrasonic transducer module. The signal generating module provides a first drive signal, the frequency of which varies within a specified range. The output module is connected electrically to the signal generating module for receiving the first drive signal therefrom, and for adjusting amplitude of the first drive signal to result in a second drive signal. The ultrasonic transducer module is connected electrically to the output module for receiving the second drive signal therefrom, and for producing ultrasounds, the frequency of which corresponds to that of the second drive signal.

4 Claims, 8 Drawing Sheets

US 7,669,478 B2

ULTRASONIC DRIVING DEVICE WITH MULTI-FREQUENCY SCANNING

BACKGROUND OF THE INVENTION

1. Field of the Invention

The invention relates to a driving device, more particularly to an ultrasonic driving device with multi-frequency scanning.

2. Description of the Related Art

Ultrasound refers to acoustic frequencies above the range audible to the human ear, or above a frequency of 20 kHz. Ultrasound is useful in many aspects. For example, an ultrasonic cleaner uses ultrasounds to excite a cleaning liquid in which articles to be cleaned are immersed. Ultrasound is even applicable in the medical field, such as in ultrasonic hyperthermia instruments. A hyperthermia instrument produces ultrasounds that are passed through the superficial and deep muscle layers via the skin in order to generate heat energy so as to achieve heat treatment effects.

FIG. 1 illustrates a conventional ultrasonic driving device 4 employed in an ultrasonic cleaner that includes a power supplying device 3, and a plurality of vibrators (not shown) immersed in a cleaning liquid. It should be noted herein that the number of vibrators can also be one. The conventional ultrasonic driving device 4 includes a signal generating module 41, an output module 42, and an ultrasonic transducer module 43. The power supplying device 3 receives an alternating current power signal from a commercial power source, and converts the alternating current power signal into a direct current operating power signal. The signal generating module 41 receives the operating power signal from the power supplying device 3, and produces an alternating current first drive signal (VD1). The output module 42 receives the operating power signal and the first drive signal (VD1) from the power supplying device 3 and the signal generator module 41, respectively, and adjusts the amplitude of the first drive signal (VD1) to result in a second drive signal (VD2).

The ultrasonic transducer module 43 is immersed in the cleaning liquid, and is responsive to the second drive signal (VD2) to produce ultrasounds, the frequency of which corresponds to that of the second drive signal (VD2). The ultrasonic transducer module 43 is made from piezoelectric ceramic elements. As the second drive signal (VD2) is received by the piezoelectric ceramic elements, electrical energy of the second drive signal (VD2) is converted into mechanical energy. In response to the second drive signal (VD2), the piezoelectric ceramic elements also generate vibrations with a frequency that corresponds to that of the second drive signal (VD2).

The ultrasounds produced by the ultrasonic transducer module 43 in the cleaning liquid result in ultrasonic vibrations that correspond in frequency to the ultrasounds. Due to the viscosity of the cleaning liquid, the ultrasonic vibrations generate microscopic cavitation bubbles in the cleaning liquid. When the microscopic cavitation bubbles break upon contact with surfaces of an article immersed in the cleaning liquid, the energy released thereby can clean debris from the surfaces of the immersed article.

As shown in FIG. 2, since the conventional ultrasonic cleaner produces ultrasounds with a fixed frequency, ultrasonic vibrations of the vibrators are limited in that particular frequency as well. However, since the vibrators are made by sintering, it is impossible to make the drive frequencies of all the vibrators uniform with each other. Consequently, using ultrasounds with a fixed frequency can only drive those vibrators whose drive frequency corresponds to the fixed frequency with an acceptable response. In other words, since not all vibrators can be driven simultaneously to generate ultrasonic vibrations in the cleaning liquid, the cleaning efficiency of the ultrasonic cleaner employing the conventional ultrasonic driving device 4 is relatively low.

SUMMARY OF THE INVENTION

Therefore, the object of the present invention is to provide an ultrasonic driving device with multi-frequency scanning, wherein the ultrasonic driving device can generate ultrasounds with frequencies that vary within a specified range.

According to the present invention, there is provided an ultrasonic driving device with multi-frequency scanning that includes a signal generating module, an output module, and an ultrasonic transducer module.

The signal generating module provides a first drive signal, the frequency of which varies within a specified range.

The output module is connected electrically to the signal generating module for receiving the first drive signal therefrom, and for adjusting amplitude of the first drive signal to result in a second drive signal.

The ultrasonic transducer module is connected electrically to the output module for receiving the second drive signal therefrom, and for producing ultrasounds, the frequency of which corresponds to that of the second drive signal.

BRIEF DESCRIPTION OF THE DRAWINGS

Other features and advantages of the present invention will become apparent in the following detailed description of the preferred embodiment with reference to the accompanying drawings, of which.

DETAILED DESCRIPTION OF THE PREFERRED EMBODIMENT

Figure 3:
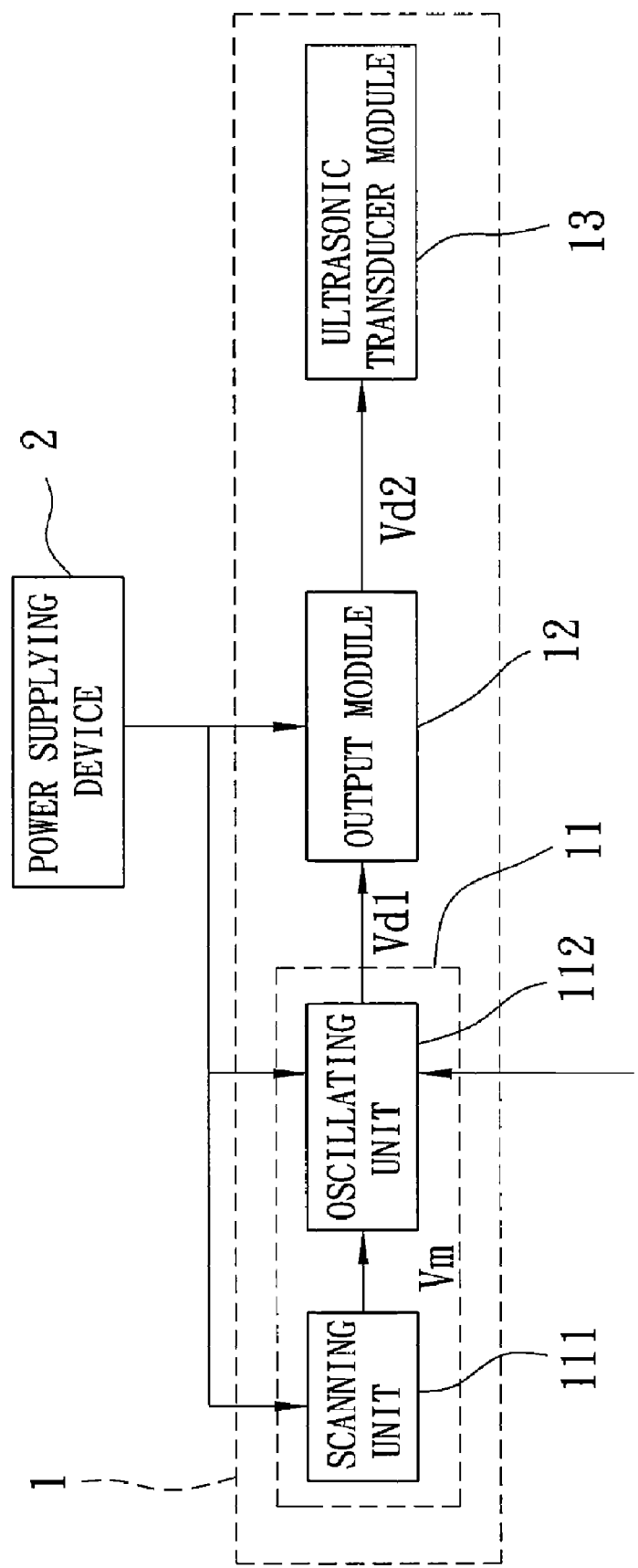
FIG. 3 is a schematic circuit block diagram of the preferred embodiment of an ultrasonic driving device with multi-frequency scanning according to the present invention.
Figure 4:
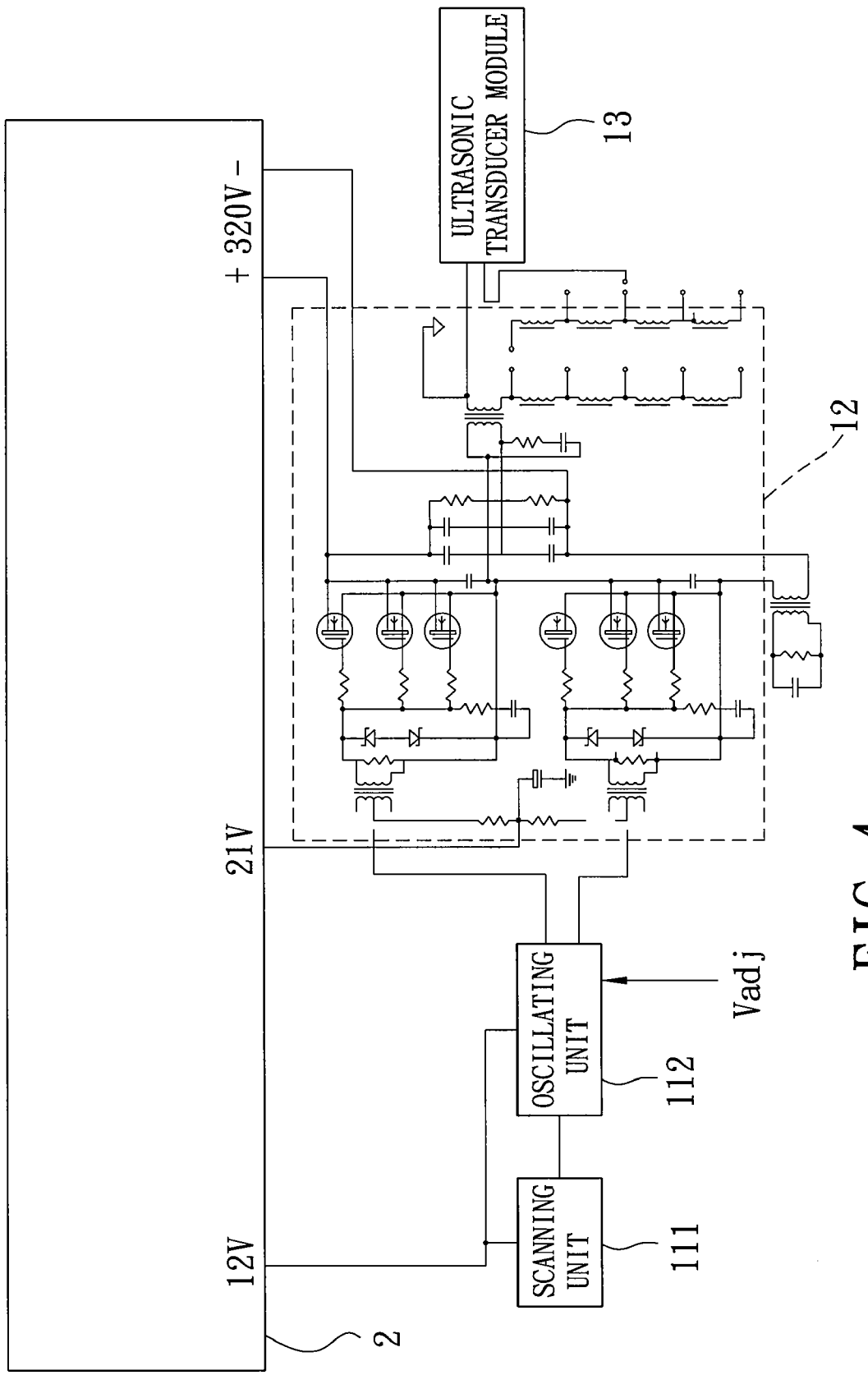
FIG. 4 is a schematic electrical circuit diagram of the preferred embodiment.
Figure 5:
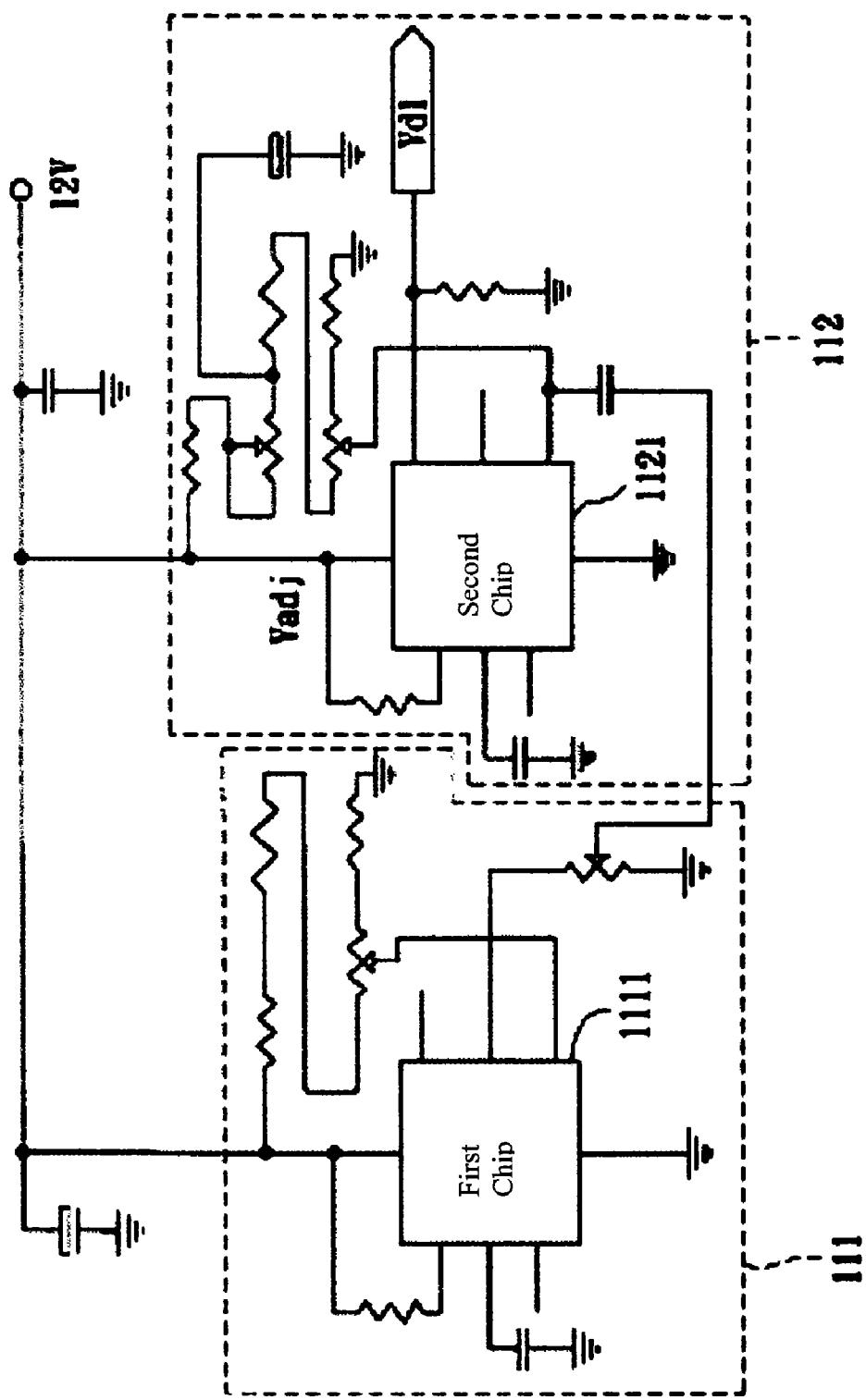
FIG. 5 is a schematic electrical circuit diagram of a scanning unit and an oscillating unit of a signal generating module according to the preferred embodiment.

As shown in FIG. 3, FIG. 4 and FIG. 5, the preferred embodiment of an ultrasonic driving device 1 with multi-frequency scanning according to the present invention generates ultrasounds adapted to drive a plurality of vibrators (not shown) to result in ultrasonic vibrations. The ultrasonic driving device 1 includes a signal generating module 11, an output module 12, and an ultrasonic transducer module 13, and is adapted to be connected electrically to an external power supplying device 2. The power supplying device 2 receives an alternating current power signal from a commercial power source, and converts the alternating current power signal into direct current operating power signals. In this embodiment, the power supplying device 2 provides a 12V direct current voltage signal to the signal generating module 11, and 21V and 320V direct current voltage signals to the output module 12. Since the feature of the present invention does not reside in the power supplying device 2, and since various circuits known in the art are capable of achieving the required functions thereof, further details of the same are omitted herein for the sake of brevity.

The signal generating module 11 provides a first drive signal (Vd1), the frequency of which varies within a specified range. The signal generating module 11 includes a scanning unit 111 and an oscillating unit 112.

The scanning unit 111 is connected electrically to the power supplying device 2 for receiving the operating power signal therefrom, and provides a voltage signal (Vm), the voltage value of which varies within a predefined range. In this embodiment, the voltage signal (Vm) is a triangular-wave voltage signal (see FIG. 6).

The oscillating unit 112 is connected electrically to the scanning unit 111 and the power supplying device 2 for receiving the voltage signal (Vm) and the operating power signal respectively therefrom. The oscillating unit 112 is adapted to receive a frequency correction signal (Vadj) from an external source, and produces a first drive signal (Vd1). The frequency of the first drive signal (Vd1) is linearly proportional to an additive voltage value of the voltage signal (Vm) from the scanning unit 111 and the frequency correction signal (Vadj). In the preferred embodiment of the present invention, the first drive signal (Vd1) is a pulse signal whose frequency varies within the specified range.

In this embodiment, the scanning unit 111 includes a first chip 1111, and the oscillating unit 112 includes a second chip 1121. Each of the first and second chips 1111, 1121 is an LM556 chip known in the art, but should not be limited thereto in other embodiments of the present invention.

The output module 12 is connected electrically to the signal generating module 11 and the power supplying device 2 for receiving the first drive signal (Vd1) and the operating power signal respectively therefrom. The output module 12 adjusts amplitude of the first drive signal (Vd1) to result in a second drive signal (Vd2).

The ultrasonic transducer module 13 is connected electrically to the output module 12 for receiving the second drive signal (Vd2) therefrom, and for producing ultrasounds. The frequency of the ultrasounds corresponds to that of the second drive signal (Vd2). In order to drive the ultrasonic transducer module 13 to produce ultrasounds, the amplitude of the second drive signal (Vd2) is required to fall within a range of between 200 and 500 Volts. In addition, the ultrasonic transducer module 13 transforms electrical energy of the second drive signal (Vd2) into mechanical energy for causing ultrasonic vibrations in the vibrators.

Since the feature of the present invention does not reside in the output module 12 and the ultrasonic transducer module 13, and since various circuits known in the art are capable of achieving the desired functions thereof, further details of the same are omitted herein for the sake of brevity.

Figure 6:
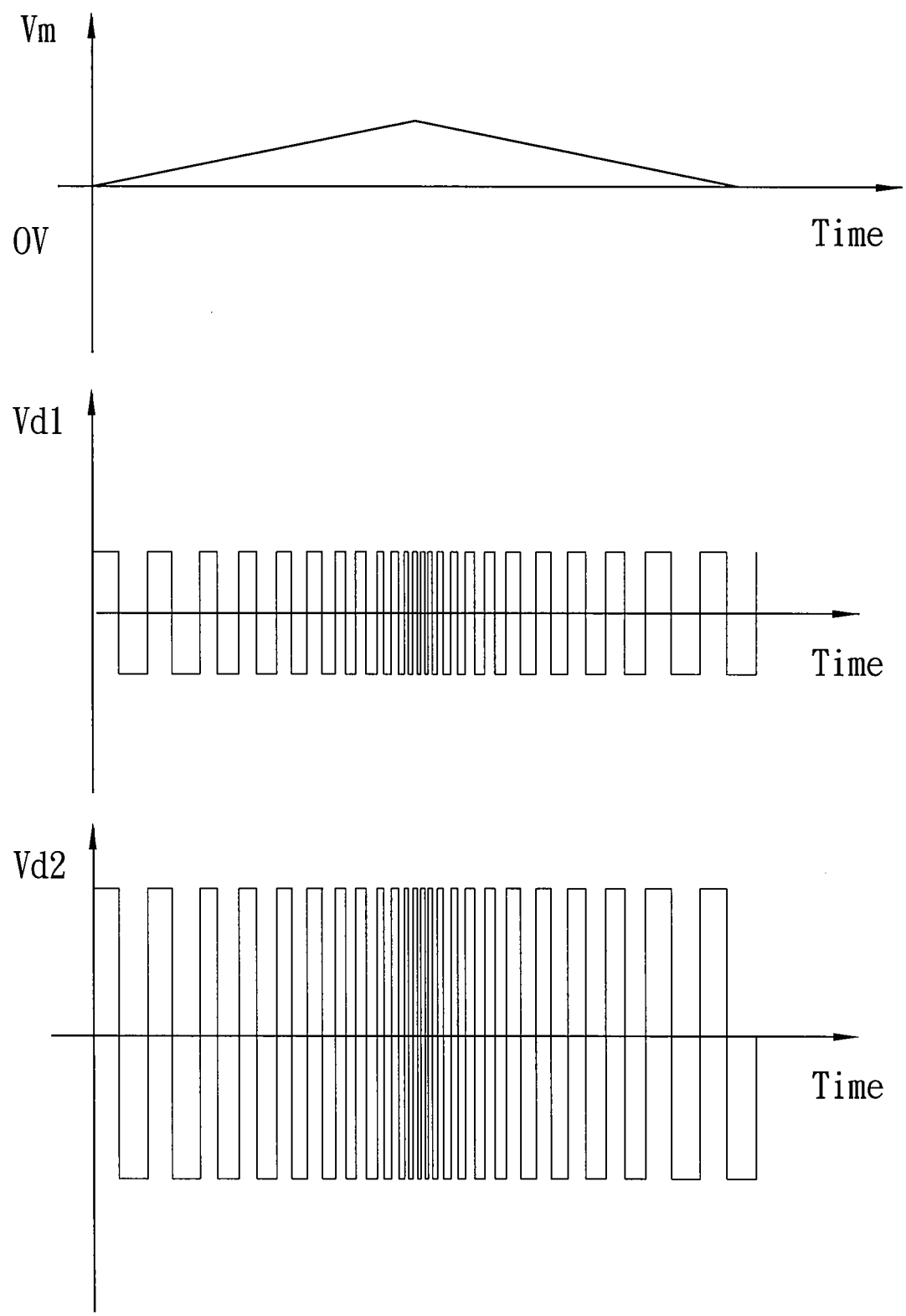
FIG. 6 is a set of wave diagrams of a triangular-wave voltage signal provided by the scanning unit, a first drive signal produced by the oscillating unit when a frequency correction signal is zero, and a second drive signal produced by an output module.

Referring to FIG. 6, it is assumed that the voltage value of the frequency correction signal (Vadj) is 0V. When the voltage value of the triangular-wave voltage signal (Vm) is 0V, the frequency of the first drive signal (Vd1) is at its minimum. As the voltage value of the triangular-wave voltage signal (Vm) increases linearly, the frequency of the first drive signal (Vd1) also increases linearly. When the voltage value of the triangular-wave voltage signal (Vm) reaches its maximum, the frequency of the first drive signal (Vd1) also reaches its maximum. The voltage value of the second drive signal (Vd2) is an amplified result of the voltage value of the first drive signal (Vd1), and is approximately 500 Volts.

Figure 7:
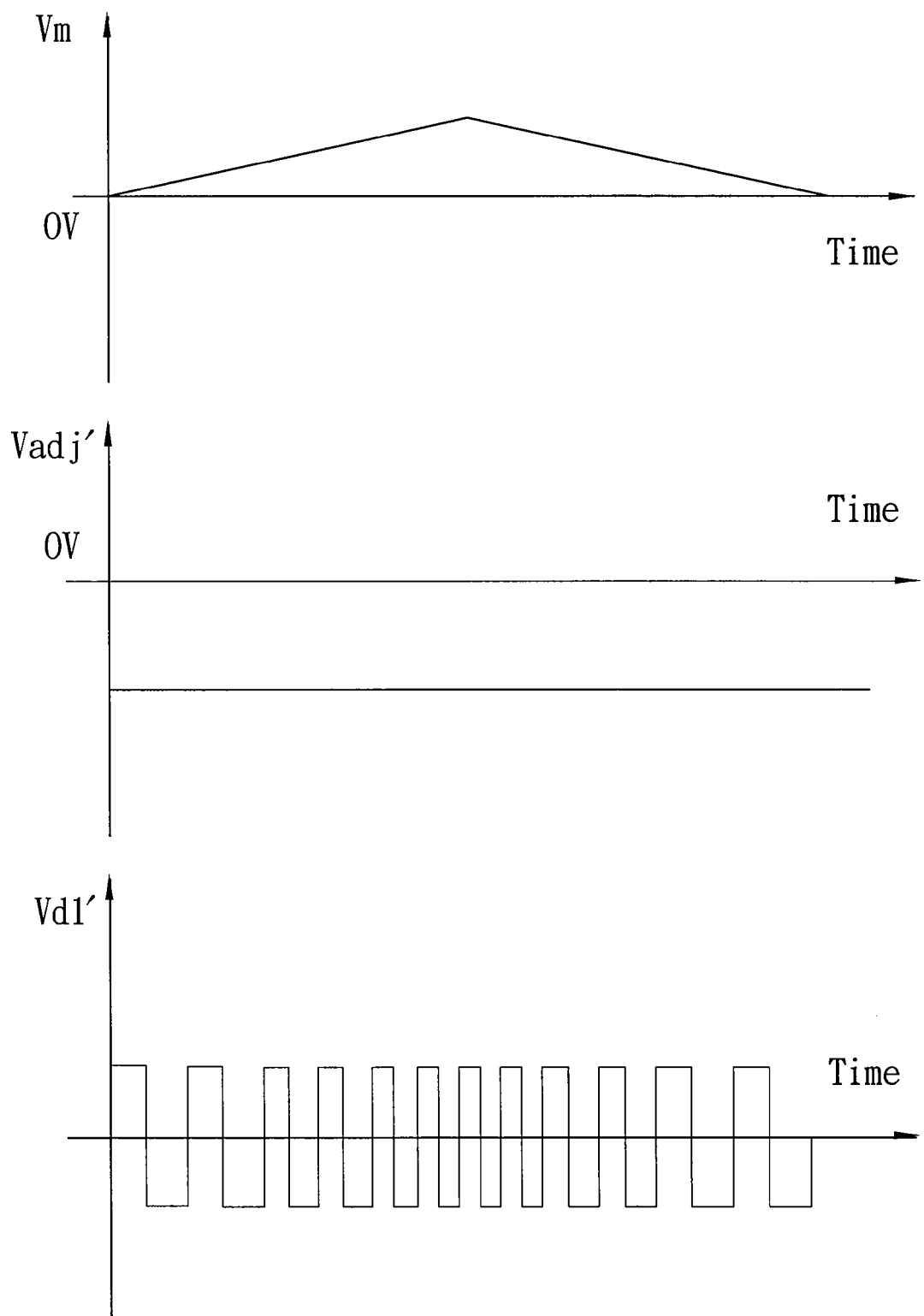
FIG. 7 is a set of wave diagrams of the triangular-wave voltage signal provided by the scanning unit, a negatively valued frequency correction signal, and the first drive signal produced by the oscillating unit when the frequency correction signal is negatively valued.

When the voltage value of the frequency correction signal (Vadj) is a negative value, then the frequency variation of the first drive signal (Vd1') would be that illustrated in FIG. 7. The first drive signal (Vd1') of FIG. 7 is the result of frequency modulating the first drive signal (Vd1) of FIG. 6 with the negatively valued frequency correction signal (Vadj). The frequency of the first drive signal (Vd1') of FIG. 7 corresponding to a 0V voltage signal (Vm) is lower than that of the first drive signal (Vd1) of FIG. 6 corresponding to a 0V triangular-wave voltage signal (Vm).

Figure 8:
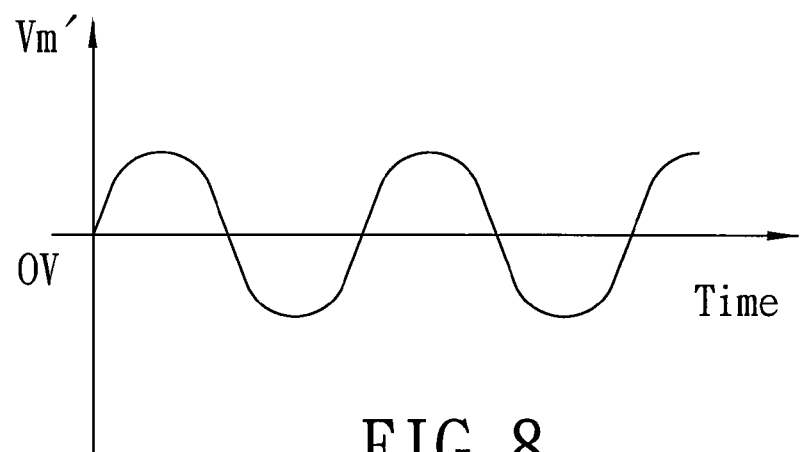
FIG. 8 is a wave diagram of a sine-wave voltage signal provided by the scanning unit.
Figure 9:
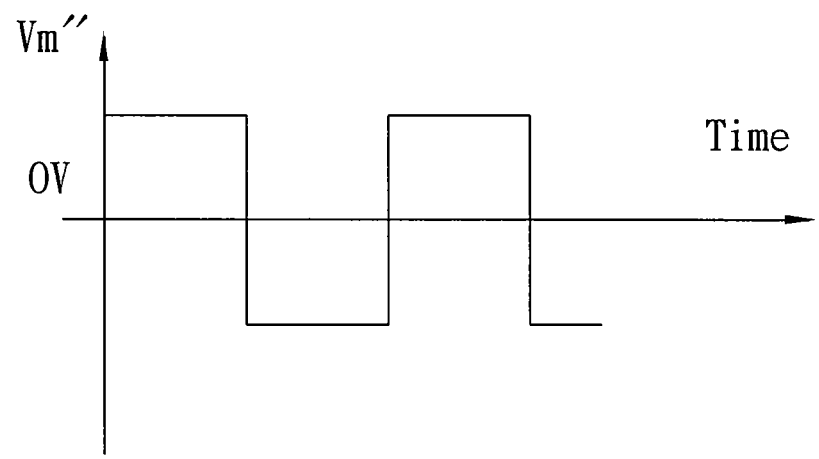
FIG. 9 is a set of wave diagrams of a square-wave voltage signal provided by the scanning unit, and the first drive signal produced by the oscillating unit when the voltage signal is a square-wave signal.
Figure 9:
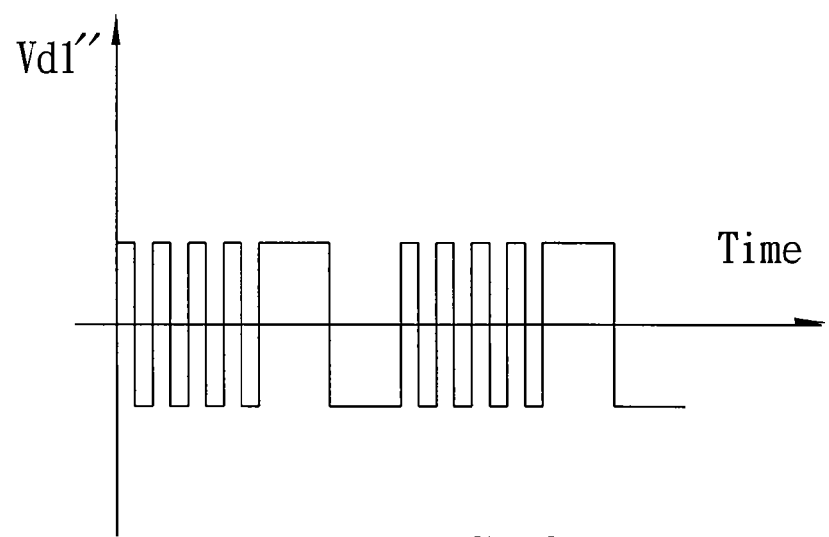

It should be noted herein that the scanning unit 111 can also provide a voltage signal having other waveforms to the oscillating unit 112, such as sine-wave or square-wave voltage signals (Vm'), (Vm") respectively illustrated in FIG. 8 and FIG. 9. Since the voltage values of a sine-wave voltage signal and a triangular-wave voltage signal both vary slowly within a specified range, when the voltage signal provided by the scanning unit 111 is a sine-wave voltage signal (Vm'), the frequency of the first drive signal ranges within a specified range as well. However, since the voltage value of a square-wave voltage signal varies between two particular values, when the voltage signal provided by the scanning unit 111 is a square-wave voltage signal (Vm"), the first drive signal (Vd1") produced by the oscillating unit 112 only has two particular frequencies, and can therefore be adapted to drive a double-vibrator.

Since the frequency of the first drive signal (Vd1) (Vd1'), (Vd1") varies within the specified range, the frequency of the ultrasounds produced by the ultrasonic transducer module 13 also varies within the specified range. Therefore, vibrators having different drive frequencies can be driven by the ultrasounds with corresponding frequencies to result in ultrasonic vibrations.

It should be noted herein that the ultrasonic driving device 1 with multi-frequency scanning according to the present invention can also be employed in ultrasonic systems other than the ultrasonic cleaners, such as ultrasonic welders and medical-use ultrasonic hyperthermia instruments.

Figure 1:
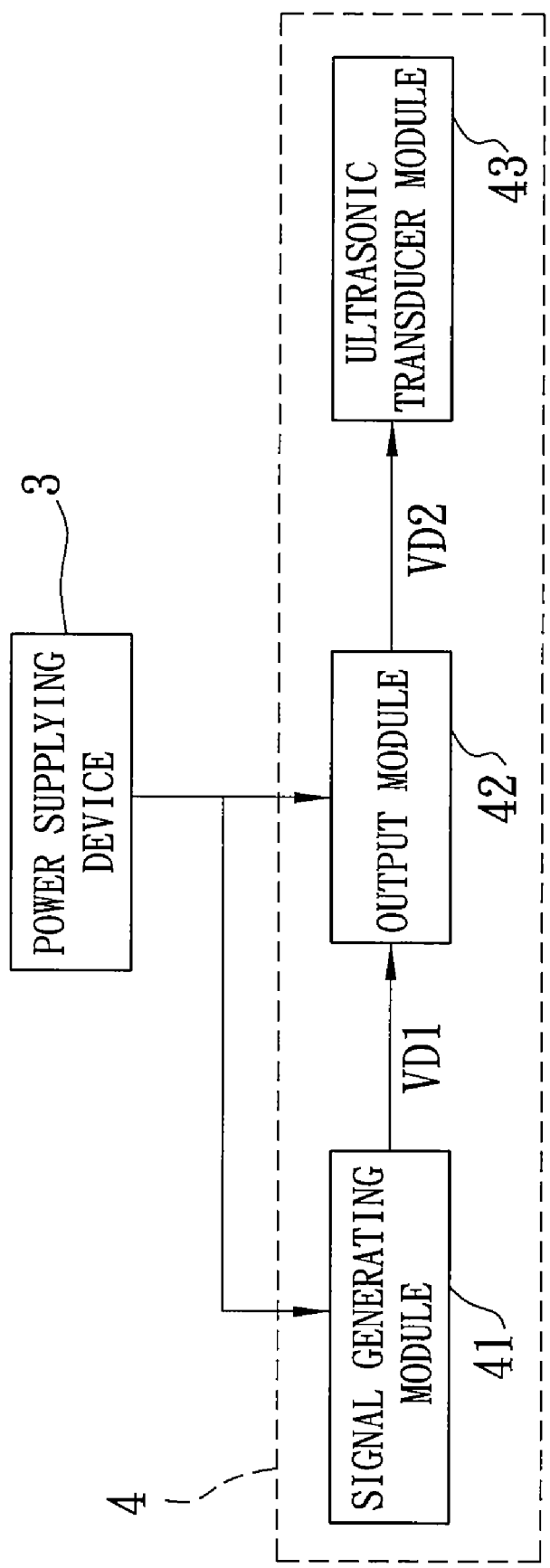
FIG. 1 is a schematic circuit block diagram of a conventional ultrasonic driving device.
Figure 2:
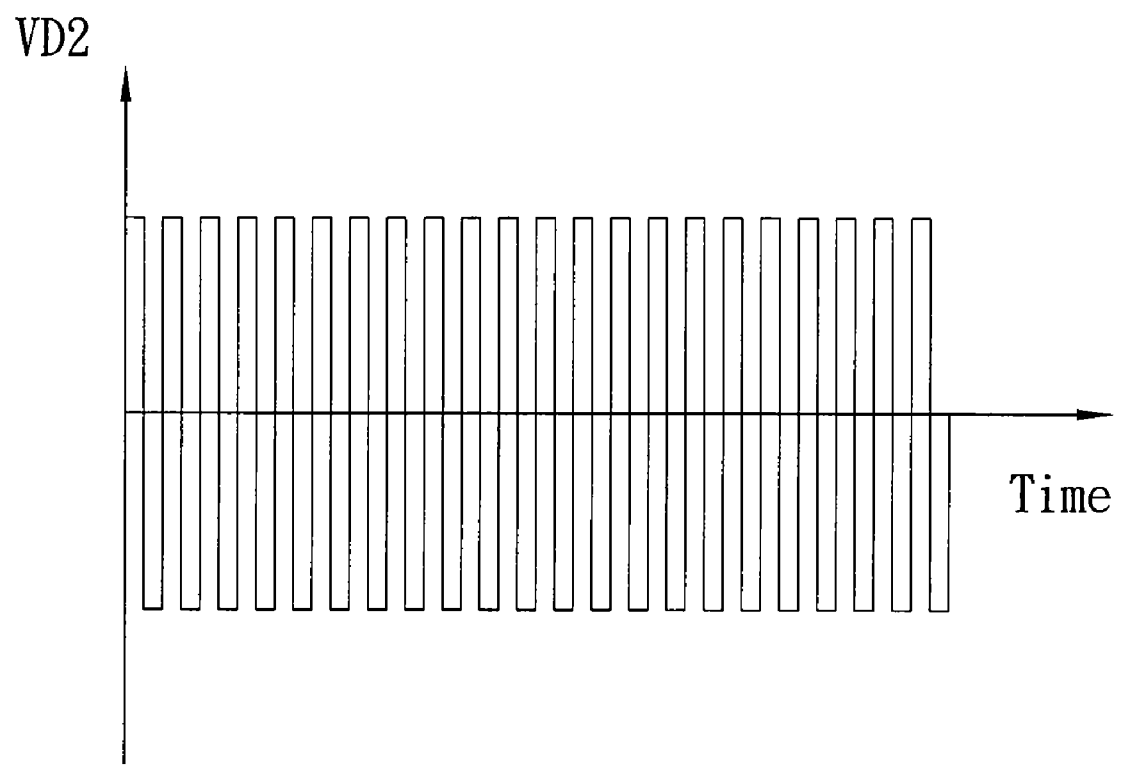
FIG. 2 is a wave diagram of a first drive signal provided by a signal generating module of the conventional ultrasonic driving device.

In sum, as compared to the conventional ultrasonic driving device 4 in the prior art (as shown in FIG. 1) that can generate ultrasounds having only one fixed frequency, the ultrasonic driving device 1 with multi-frequency scanning according to the present invention is capable of generating ultrasounds whose frequency varies within a specified range, such that the ultrasonic driving device 1 with multi-frequency scanning can be adapted to drive vibrators having different drive frequencies to result in ultrasonic vibrations. Consequently, the cleaning efficiency of an ultrasonic cleaner employing the ultrasonic driving device 1 according to the present invention is better than that employing the conventional ultrasonic driving device 4.

While the present invention has been described in connection with what is considered the most practical and preferred embodiment, it is understood that this invention is not limited to the disclosed embodiment but is intended to cover various arrangements included within the spirit and scope of the broadest interpretation and equivalent arrangements.

What is claimed is:

1. An ultrasonic driving device with multi-frequency scanning, comprising:
    a signal generating module for providing a first drive signal, the frequency of which varies within a specified range;
    an output module connected electrically to said signal generating module for receiving the first drive signal therefrom, and for adjusting amplitude of the first drive signal to result in a second drive signal; and
    an ultrasonic transducer module including a plurality of vibrators, connected electrically to said output module for receiving the second drive signal therefrom, and for producing ultrasounds, the frequency of which corresponds to that of the second drive signal, wherein the second drive signal drives the plurality of vibrators evenly.

2. The ultrasonic driving device with multi-frequency scanning as claimed in claim 1, wherein said signal generating module includes
    a scanning unit for providing a triangular-wave voltage signal, the voltage value of which varies within a predefined range; and
    an oscillating unit connected electrically to said scanning unit for receiving the voltage signal therefrom, said oscillating unit receiving a frequency correction signal from an external source, and producing the first drive signal, the frequency of which is linearly proportional to an additive voltage value of the voltage signal from said scanning unit and the frequency correction signal.

3. The ultrasonic driving device with multi-frequency scanning as claimed in claim 1, wherein said signal generating module includes:
    a scanning unit for providing a sine-wave voltage signal; and
    an oscillating unit connected electrically to said scanning unit for receiving the voltage signal therefrom, said oscillating unit receiving a frequency correction signal from an external source, and producing the first drive signal, the frequency of which is linearly proportional to an additive voltage value of the voltage signal from said scanning unit and the frequency correction signal.

4. The ultrasonic driving device with multi-frequency scanning as claimed in claim 1, wherein said signal generating module includes:
    a scanning unit for providing a square-wave voltage signal; and
    an oscillating unit connected electrically to said scanning unit for receiving the voltage signal therefrom, said oscillating unit receiving a frequency correction signal from an external source, and producing the first drive signal, the frequency of which is linearly proportional to an additive voltage value of the voltage signal from said scanning unit and the frequency correction signal.

* * * * *